United States Patent

Shalon et al.

[11] Patent Number: 5,951,873
[45] Date of Patent: Sep. 14, 1999

[54] CHROMATOGRAPHIC DEVICE WITH PISTON LOCKING MECHANISM AND METHOD OF PACKING SAME

[75] Inventors: Yehuda Shalon; Danny Meyer, both of St. Louis; Y. Andrew Li, St. Ann, all of Mo.

[73] Assignee: MODcol Corporation, St. Louis, Mo.

[21] Appl. No.: 08/996,973

[22] Filed: Dec. 23, 1997

[51] Int. Cl.⁶ ..................................... B01D 15/08
[52] U.S. Cl. ........................... 210/656; 210/198.2
[58] Field of Search ..................... 210/635, 656, 210/657, 659, 198.2, 232, 238; 141/12, 73, 80; 95/82; 96/101

[56] References Cited

U.S. PATENT DOCUMENTS

| | | | |
|---|---|---|---|
| D. 285,290 | 8/1986 | Shalon et al. | D10/81 |
| 4,350,595 | 9/1982 | Gunkel | 210/656 |
| 4,361,482 | 11/1982 | Teetz et al. | 210/198.2 |
| 4,451,365 | 5/1984 | Sättler et al. | 210/198.2 |
| 4,597,866 | 7/1986 | Couillard | 210/198.2 |
| 4,675,105 | 6/1987 | Martin et al. | 210/198.2 |
| 4,710,289 | 12/1987 | Wermuth et al. | 210/198.2 |
| 4,719,011 | 1/1988 | Shalon et al. | 210/198.2 |
| 4,737,292 | 4/1988 | Ritacco et al. | 210/656 |
| 4,769,141 | 9/1988 | Couillard | 210/198.2 |
| 4,865,728 | 9/1989 | Larsson | 210/198.2 |
| 4,882,047 | 11/1989 | Shalon | 210/198.2 |
| 4,891,133 | 1/1990 | Colvin, Jr. | 210/198.2 |
| 5,137,628 | 8/1992 | Hart et al. | 210/198.2 |
| 5,169,522 | 12/1992 | Shalon et al. | 210/198.2 |
| 5,192,433 | 3/1993 | Shalon | 210/198.2 |
| 5,213,683 | 5/1993 | Mann | 210/198.2 |
| 5,366,621 | 11/1994 | Bidell | 210/198.2 |
| 5,378,361 | 1/1995 | Baeckstrum | 210/198.2 |
| 5,423,982 | 6/1995 | Jungbauer et al. | 210/198.2 |
| 5,462,659 | 10/1995 | Saxema et al. | 210/198.2 |
| 5,531,810 | 7/1996 | Fullemann | 210/198.2 |

*Primary Examiner*—Ernest G. Therkorn
*Attorney, Agent, or Firm*—Howell & Haferkamp, L.C.

[57] ABSTRACT

A chromatographic device comprising a column body having a first end and a closed second end. The device further includes a piston inside the column body, a chromatographic medium, a rod, and a locking mechanism. The chromatographic medium is within the column body and between the piston and the second end. The rod has a longitudinal rod axis and is operatively engageable with the piston for pressing the piston in the column body. The locking mechanism is adapted for locking the rod relative to the column body in a manner to prevent movement of the rod relative to the column body in an outward longitudinal direction away from the piston without preventing movement of the rod relative to the column body in an inward longitudinal direction toward the piston. Preferably, the chromatographic device includes a spring for exerting a constant axial compression against the piston to prevent the formation of voids in the packing medium.

3 Claims, 4 Drawing Sheets

_5,951,873_

CHROMATOGRAPHIC DEVICE WITH PISTON LOCKING MECHANISM AND METHOD OF PACKING SAME

BACKGROUND OF THE INVENTION

This invention relates to the liquid chromatography, and more particularly to chromatographic devices having pistons for compressing a chromatographic medium.

Chromatography is a method for separating individual compounds in a mixture by distributing the compounds between heterogenous phases. A column packing material (or media), forming a stationary phase, generally has a large surface area through which a liquid mobile phase is allowed to flow. Chemical compounds in the mobile phase are maintained in the system for a time that is dependent upon the affinity of the particular compounds for the stationary phase. Multiple component mixtures can, with chromatography, be separated into single components in a single step procedure.

Chromatographic separations can be carried out efficiently in columns slurry packed with microparticulate media. The slurry is uniformly and rapidly compacted into a column under pressure. The slurry is maintained at very high pressure and density to achieve the most efficient end results.

A chromatographic device includes a chromatographic column (having a cylindric column body and a fixed end plate covering one end of the column body), a piston slidable within the column body, an intake opening through the piston, a discharge opening through the end plate, a first porous frit seated within a frit-receiving socket of the piston and covering the intake opening, and a second porous frit secured to the end plate and covering the discharge opening. A slurry containing the packing material, such as a granular silica or polymeric media, is placed within the column body and the piston is moved toward the fixed end plate to compress the slurry. The pores of the frits are sized to permit the liquid of the slurry to flow out the discharge opening while preventing discharge of the packing material. Conventionally, when the chromatographic media within a chromatographic column is packed, a telescoping rod of a hydraulic pushing device pushes the piston into the column. This compression packs the packing material to a predetermined pressure (which may typically be around 1,000 to 5,000 p.s.i., but these values are merely exemplary rather than limiting).

With such conventional method of packing chromatographic columns, the column remains attached to the pushing device so that the rod of the hydraulic pushing device maintains the pushing force on the piston. In other words, the column must remain attached to the pushing device during operation of the chromatographic column, i.e., during chromatographic separations.

SUMMARY OF THE INVENTION

Among the several objects of the present invention may be noted the provision of an improved method and apparatus for packing chromatographic columns; the provision of such a method and apparatus for packing a chromatographic column in which compression is maintained on a column piston even after removal of the column from a pushing device; the provision of such a method and apparatus in which the column is permitted to move in an axial direction to compress a chromatographic medium in the column but is prevented from moving in an opposite direction; and the provision of such a method and apparatus in which an elastic force is applied to the piston even after removal of the chromatographic column from the pushing device.

In general, a chromatographic device of the present invention comprises a longitudinally extending tube having a first end and a second end, the second end being closed, a piston inside the hollow tube, a chromatographic medium, a rod, and a locking mechanism. The chromatographic medium is within the tube and between the piston and the second end. The rod has a longitudinal rod axis and is operatively engageable with the piston for pressing the piston in the hollow tube. The locking mechanism is adapted for locking the rod relative to the tube in a manner to prevent movement of the rod relative to the tube in an outward longitudinal direction away from the piston without preventing movement of the rod relative to the tube in an inward longitudinal direction toward the piston.

Another aspect of the present invention is a method of packing a chromatographic medium in a longitudinally extending chromatographic tube. The tube has a first end and a second end, the second end being opposite the first end and closed. The method comprises: placing the chromatographic medium in the chromatographic tube; inserting a piston into the tube, the chromatographic medium being between the piston and the closed second end of the tube; placing a pushing assembly adjacent the piston, the pushing assembly having a locking mechanism adapted for permitting the piston to move in a first longitudinal direction toward the closed second end of the tube and for preventing the piston to move in a second longitudinal direction toward the first end of the tube; applying a compressive force in the first longitudinal direction against the pushing assembly to move the piston toward the closed second end of the tube to compress the chromatographic medium; and removing the compressive force from the pushing assembly, the locking mechanism locking against movement of the piston in the second longitudinal direction.

Other objects and features will be in part apparent and in part pointed out hereinafter.

DESCRIPTION OF THE PREFERRED EMBODIMENTS

Figure 1:
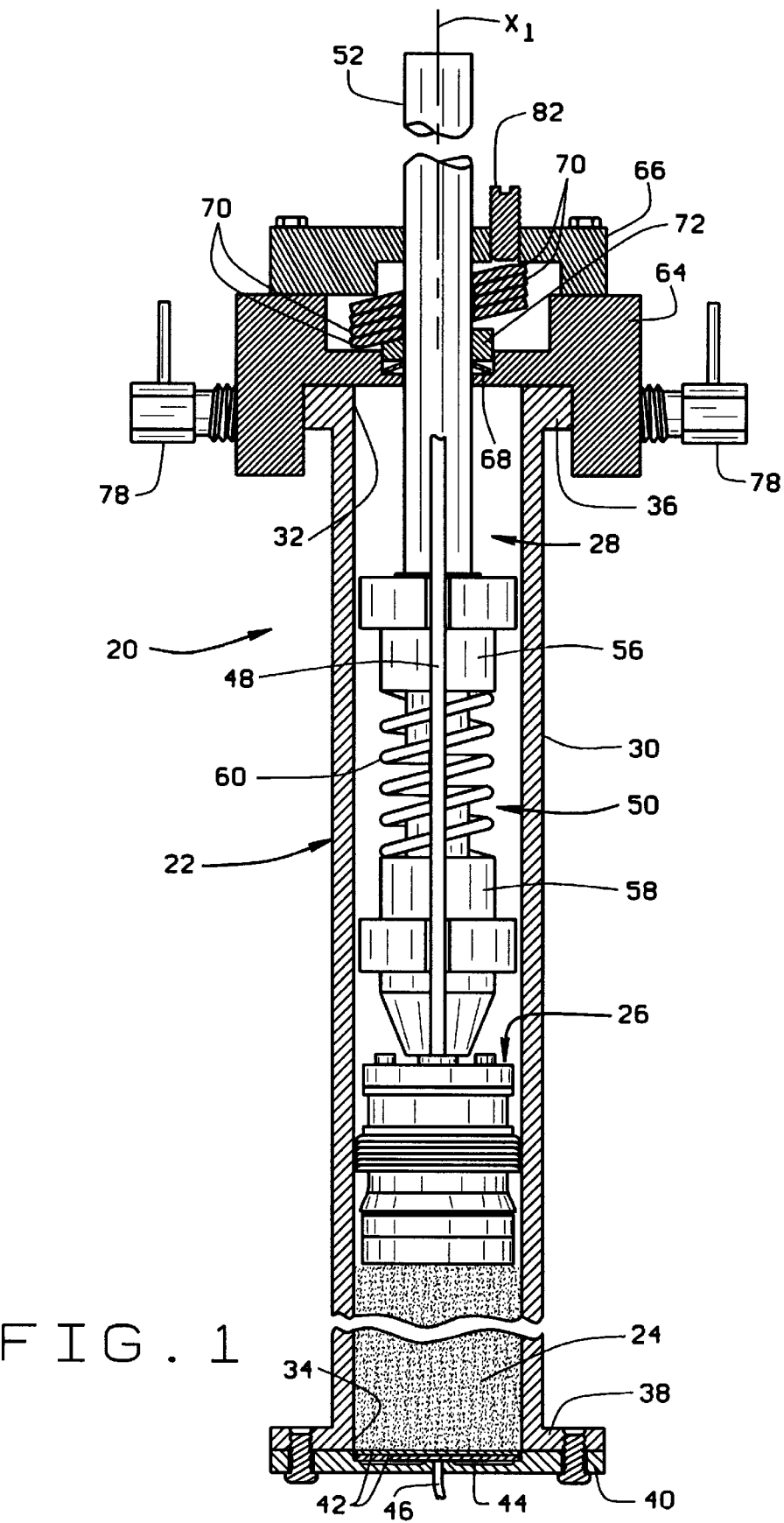
FIG. 1 is a front elevational view of a chromatographic device of the present invention in partial section, the chromatographic device including a column body, a chromatographic medium, a piston, and a pushing assembly.
Figure 2:
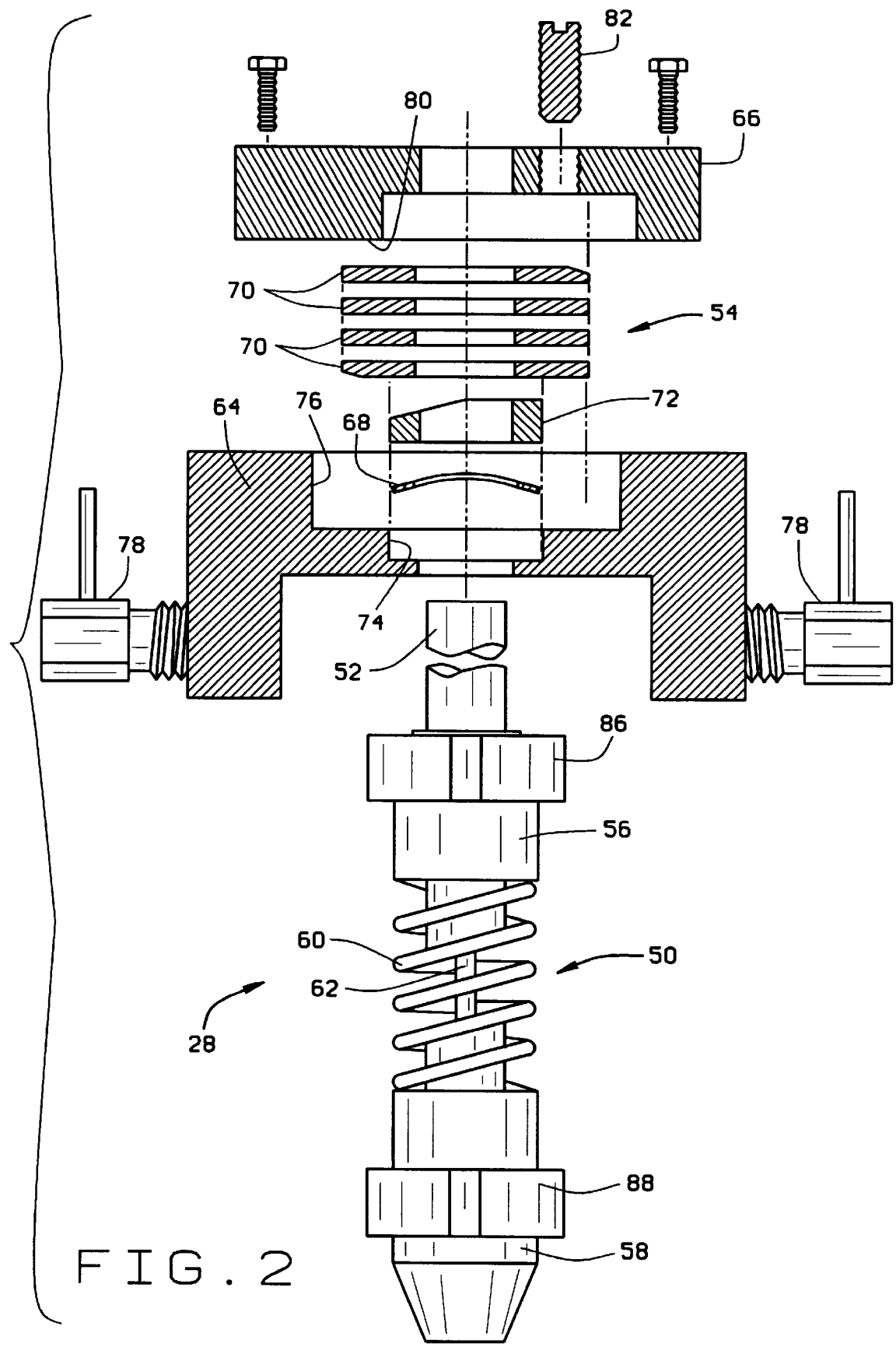
FIG. 2 is an enlarged exploded front elevational view of the pushing assembly of FIG. 1 with some parts shown in section.

Referring now to the drawings, and first more particularly to FIG. 1, a chromatographic device of the present invention is indicated in its entirety by the reference numeral 20. The chromatographic device includes a tubular column body, generally indicated at 22, a chromatographic medium 24, a piston 26, and a pushing assembly, generally indicated at 28. Preferably, the column body 22, chromatographic medium 24, and piston 26 are substantially the same as those described in U.S. patent application Ser. No. 08/942,153, filed Oct. 1, 1997 and entitled Apparatus That Maintains Compression in a Tube, incorporated herein by reference.

The column body 22 comprises a longitudinally extending tube 30 having a first end 32 (the upper end as viewed in FIG. 1) and a second end 34 (the lower end as viewed in FIG. 1) opposite the first end. A first (upper) flange 36 circumscribes the tube 30 at the first end 32, and a second (lower) flange 38 circumscribes the tube at the second end 34. The upper and lower flanges 36, 38 preferably are rectangular, and more preferably are square. An end plate 40 closes the lower end 34 of the tube 30 and is secured to the lower flange 38. The end plate 40 is shaped and configured for holding one or more porous frits 42, and includes a plurality of radial grooves 44 and a discharge opening for receiving an outlet tube 46. The piston 26 is moveable within the tube 30 of the column body 22. The piston 26 also includes frits (not shown) similar to frits 42. The frits allow passage of a fluid containing substances in solution to be separated while not allowing solid particles in the chromatographic medium (usually, but not necessarily, fine silica particles) to escape from the column body 22. The solution is supplied through a feeding tube 48 secured to the piston 26 and in fluid communication with a passageway (not shown) extending through the piston. It is to be understood that the designation of one of the tubes as a "feeding" tube and the other as an "outlet" tube is arbitrary, inasmuch as the chromatographic device 20 is capable of being operated with fluid flowing through it in either direction.

Referring now to FIGS. 1–5, the pushing assembly 28 comprises a spring assembly, generally indicated at 50, a rod 52, and a locking mechanism, generally indicated at 54. As described in greater detail below, the pushing assembly 28 is configured to be positioned against the piston 26 in a manner such that application of a compressive force (i.e., a downward force as shown in FIG. 1) on the rod 52 moves the piston downward to pack the chromatographic medium 24.

The spring assembly 50 includes an upper and lower spring engaging members 56, 58, and a helical spring 60. The upper and lower spring engaging members 56, 58 engage opposite ends of the spring 60 and are held together by a small connecting rod 62 (FIG. 2) extending through the spring. The connecting rod 62 is secured at its lower end to the lower spring engaging member 58 and extends upwardly through a bore (not shown) in the upper spring engaging member 56. Except for the compressive force of the spring 60, the upper spring engaging member 56 is free to slide along the connecting rod 62. The upper end of the connecting rod 62 includes a head (not shown) having a diameter larger than that of the bore and engageable with the upper member 56 to limit upward movement of the upper member relative to the lower member 58. Preferably, the spring 60 is at least slightly compressed in the assembled spring assembly 50 to bias the upper member 56 against the head. The spring engaging members 56, 58 therefore move toward each other only upon compression of the spring 60.

The rod 52 preferably has a smooth, continuous outer surface. In other words, the rod 52 preferably is not knurled, grooved, etc. The rod 52 is secured at its lower end to the upper spring engaging member 56 by a threaded fastener (not shown) or by some other suitable fastening means. The rod 52 extends upward through the locking mechanism 54.

The locking mechanism 54 includes a base member 64, a cover plate 66, a belville spring 68, four rectangular locking plates (or members) 70, and a canting member 72. The locking mechanism 54 is configured for locking the rod 52 relative to the base member 64 in a manner to prevent movement of the rod relative to the base member in an outward longitudinal direction (up as viewed in FIG. 1) away from the piston without preventing movement of the rod relative to the base member in an inward longitudinal direction (down as viewed in FIG. 1) toward the piston. The base member 64 includes a bore 74 sized for receiving the belville spring 68 and the canting member 72, and a cavity 76 above the bore 74 for receiving the locking plates 70 in a face-to-face orientation. The base member 64 is releasably secured to the upper flange 36 of the column body 22 via four pin-type fasteners 78 (only two of which are shown). Preferably, the pin-type fasteners 78 are of the type manufactured by Vlier Inc., 40 Guest Street, Brighton, Mass., under the description full travel hand-retractable plungers. The fasteners 78 include retractable pins (not shown) adapted to be laterally inserted into horizontal bores (not shown) in the upper flange 36.

The base member 64, canting member 72, locking plates 70 and cover plate 66 have cylindric bores for extension of the rod 52 therethrough. The cover plate 66 is secured to the base member 64 via suitable fasteners to hold the base member, spring 68, canting member 72, and locking plates 70 together with their cylindric bores aligned so that the rod extends therethrough along a longitudinal axis $X_1$. The cover plate 66 has a shoulder 80 engageable with an end margin of the upper-most locking plate (the left end margin as viewed in FIGS. 3–5). The canting member has a slanted upper surface engageable with the underside of the lower-most locking plate 70. Preferably, the locking plates 70 are planar members and are of hardened steel. The locking plates 70 are angularly moveable relative to the axis $X_1$ and relative to the base member 64 between a locking position (shown in FIG. 3) and an unlocking position (shown in FIG. 4). Each locking plate 70 has a locking plate axis $X_2$ (only one of which is shown for simplicity). The longitudinal axis $X_1$ and the rod axis $X_2$ define a first angle $A_1$ (FIG. 3) when the locking plates 70 are in their locking position and define a second angle $A_2$ (FIGS. 4 and 5) when the locking plates 70 are in their unlocking position. The first and second angles are both acute. However, second angle $A_2$ is closer to 90 degrees than is the first angle $A_1$. When the locking plates 70 are in their locking position, they press laterally against the rod 52 sufficient to prevent movement of the rod along the longitudinal axis $X_1$ relative to the base member 64 and column body 22. When the locking plates 70 are in their unlocking position, the cylindric bores through the locking plates align sufficiently with the rod 52 to permit movement of the rod along the longitudinal axis $X_1$.

Figure 3:
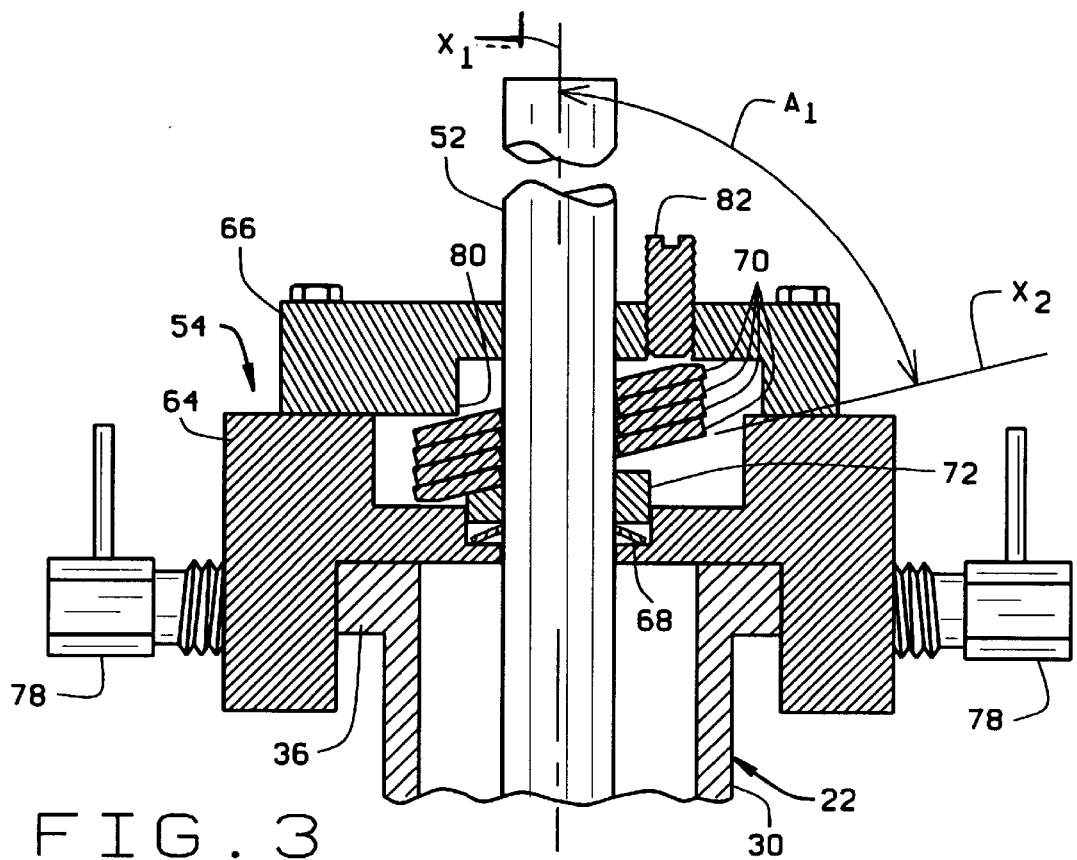
FIG. 3 is a fragmented front elevational view, in section, showing a locking mechanism of the pushing assembly positioned to prevent movement of a rod of the locking mechanism away from the piston.

As shown in FIG. 3, the canting member 72, spring 68, and shoulder 80 bias the locking plates 70 in their locking position to prevent upward movement of the rod 52 relative to the base member 64 and attached column body 22.

Figure 4:
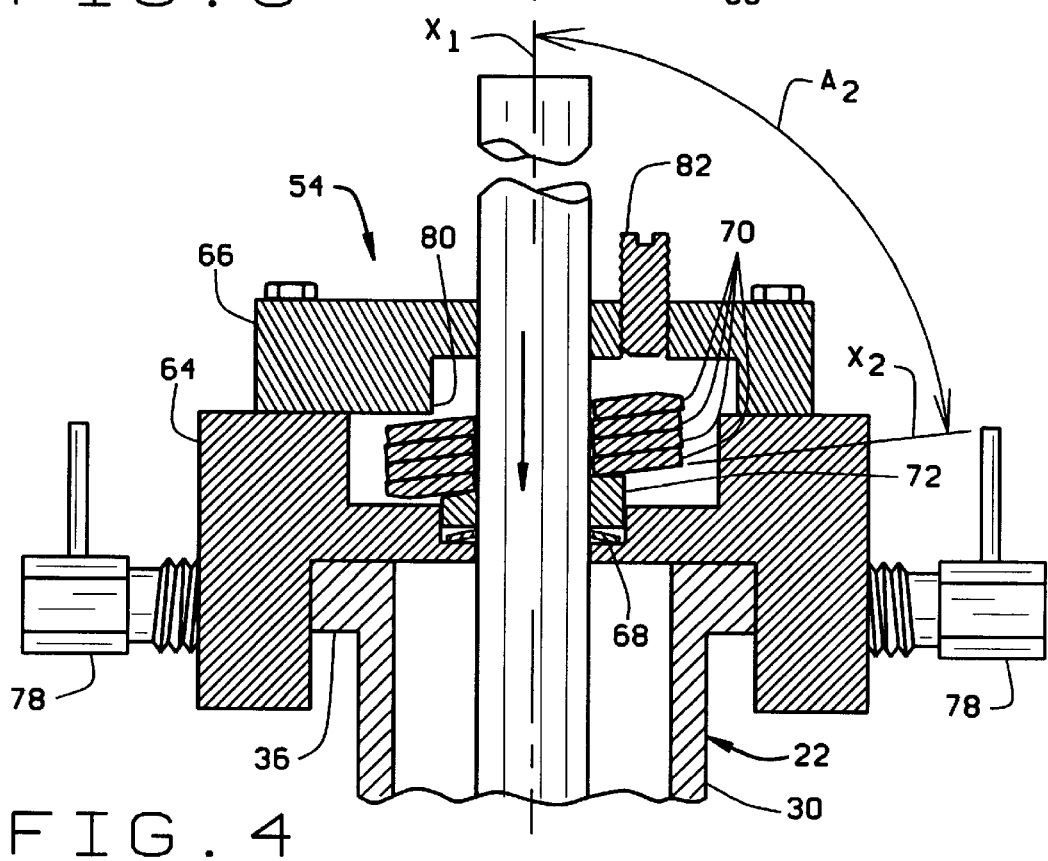
FIG. 4 is a fragmented front elevational view, in section, similar to that of FIG. 3 but showing the position of the locking mechanism as the rod is being pushed toward the piston.

Although the spring 68 is preferably a belville spring 68, it is to be understood that other compressible springs may be employed without departing from the scope of this invention. When an upwardly directed force is applied to the rod 52, the frictional force between the rod and the locking plates 70 and the pressing force between the shoulder 80 and the upper-most locking plate tends to rotate the plates in a counter-clockwise direction as viewed in FIG. 3 to thereby increase the locking action of the locking plates against the rod. Thus, the greater the upwardly directed force against the rod 52, the greater the locking action of the locking plates 70 against the rod. Referring now to FIG. 4, the locking mechanism 54 does not prevent downward movement of the rod 52 relative to the base member 64. When a downwardly directed force is applied to the rod 52, the frictional force between the rod and locking plates and the pressing force between the lower-most locking plate and the base member 64 tends to rotate the plates in a clockwise direction as viewed in FIG. 4 to thereby decrease the locking action of the locking plates against the rod. When the locking plates have rotated to unlocking position shown in FIG. 4, the locking mechanism permits downward movement of the rod relative to the base member 64. Because of the configuration of the locking mechanism 54, application of a sufficient downward force automatically moves the locking plates 70 to their unlocking position.

Figure 5:
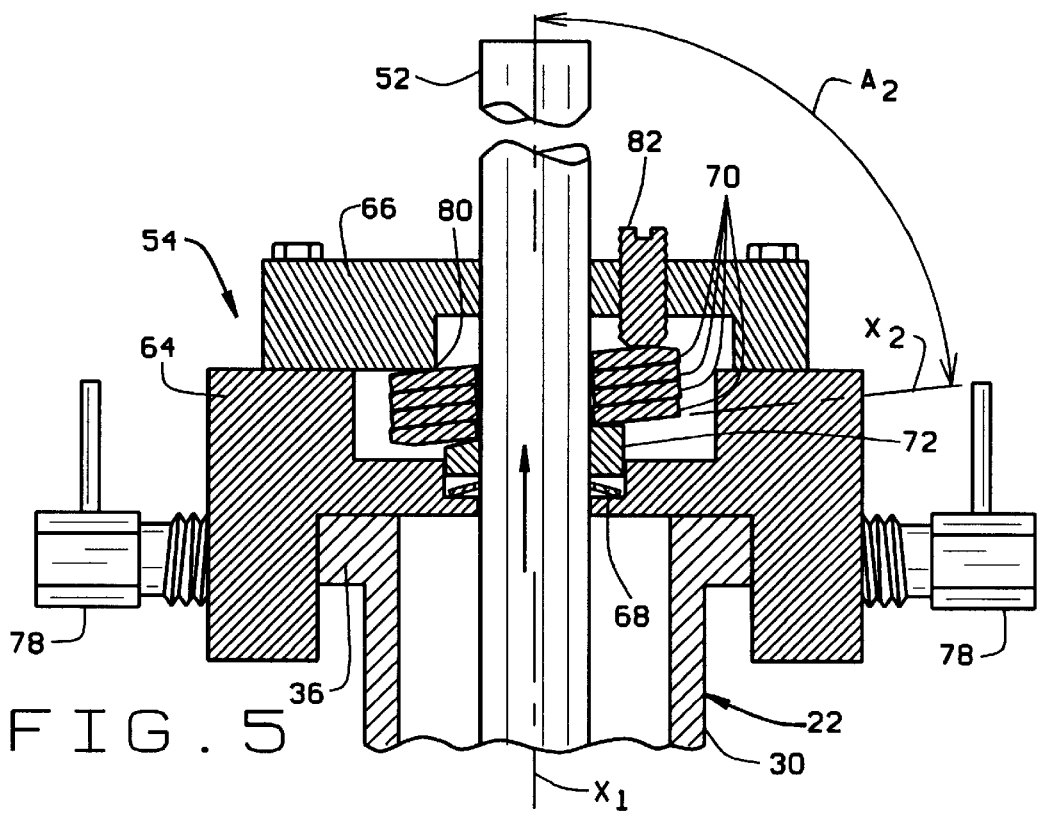
FIG. 5 is a fragmented front elevational view, in section, similar to that of FIGS. 3 and 4, but showing a release member positioned to permit the rod to move away from the piston.

Referring now to FIG. 5, the locking mechanism 54 preferably has a release screw 82. The release screw 82 is threaded through the cover plate 66. Threading of the release screw 82 downward causes the screw to push against the upper-most locking plate 70 to thereby cause the locking plates to rotate clockwise to their unlocking position. With the screw 82 so positioned, the locking mechanism 54 permits up and down movement of the rod 52 relative to the base member 64 and column body 22 along the longitudinal axis $X_1$.

Figures 6, 7:
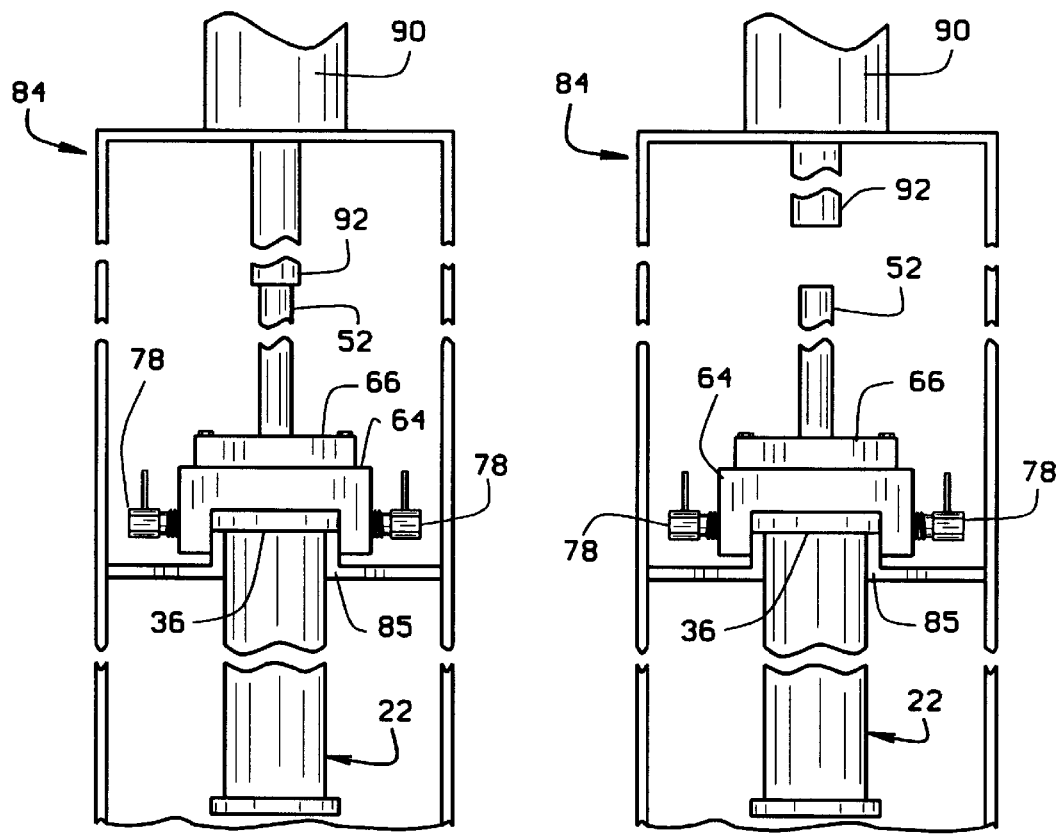
FIG. 6 is a fragmented front elevational view of the chromatographic device of FIG. 1 attached to a hydraulically operated pushing device having a hydraulically operated rod engaging the rod of the pushing assembly.
FIG. 7 is a fragmented front elevational view similar to FIG. 6 but showing the hydraulically operated rod in a retracted position and spaced above the rod of the pushing assembly.

In operation, the column body 22 is placed on a pushing device, such as the compression apparatus 86 (FIGS. 6 and 7), with the upper flange 36 of the column body supported on a column receiving portion 85 of the compression apparatus. Chromatographic medium 24 is then poured or otherwise placed into the tube 30 of the column body 22 via the upper end 32 of the tube. Next, the piston 26 is inserted into the tube 30 and pushed downward toward the medium 24. The pushing assembly 28 is then positioned with the spring assembly 50 inserted into the tube 30 of the column body 22 and the base member 64 placed over the upper end 32 of the tube and secured to the upper flange 36. Preferably, the spring assembly 50 includes upper and lower disc-shaped guide blocks 86, 88. The upper guide block 86 is secured to the upper spring engaging member 56 and the lower guide block 88 is secured to the lower spring engaging member 58. The guide blocks 86, 88 keep the spring engaging member 56 centered within the tube. The guide blocks 86, 88 are configured to slide within the tube 30 and are preferably made of polytetrafluoroethylene. Preferably, the guide blocks 56, 58 include slots for passage of the feeding tube 48 therethrough. The underside of the lower spring engaging member 58 is brought into engagement with the upperside of the piston 26. The rod 52 of the pushing assembly 28 extends upward through the locking mechanism 54 and its longitudinal axis $X_1$ is coaxial with the axis of the column body 22.

The compression apparatus 84 includes a hydraulic cylinder 90 having a pushing rod 92. The pushing rod 92 has a longitudinal axis which is aligned with the axis $X_1$ of the rod 52 of the pushing assembly 28. The pushing rod 92 is hydraulically driven along the axis $X_1$ between raised and lowered positions. The pushing rod 92 is driven downward against the upper end of the rod 52 of the pushing assembly 28 to press the spring assembly against the piston 26 to thereby drive the piston downward against and pack the chromatographic medium 24. The locking mechanism 54 permits downward (inward) movement of the rod 52 relative to the column body 22. After the chromatographic medium 24 is sufficiently packed, the pushing rod 92 is driven upward away from the rod 52 of the pushing assembly 28. The locking mechanism 54 prevents upward movement of the rod 52 relative to the column body 22 and relative to the base member 64. The downward movement of the rod 52 through the column body 22 caused the spring 60 to compress and thereby exert an elastic force on the piston 26 to press the piston against the chromatographic medium. Because the rod 52 is locked against upward movement relative to the column body 22, the spring 60 remains compressed even after the pushing rod 92 of the compression apparatus 84 is raised. Thus, the spring 60 of the pushing assembly 28 maintains a pushing force (i.e., constant axial compression) against the piston 26 to prevent the formation of voids in the packing medium 24. After the pushing rod 92 is raised, the assembled chromatographic device 20 may be removed from the compression apparatus 84 and then used for a chromatographic separation operation at a location remote from the compression apparatus.

If it is desired to remove the pushing assembly 28 from the column body 22, the release screw 82 is screwed down to move the locking plates 70 to their unlocking positions, and the rod 52 may then be pulled upwardly through the locking mechanism 54.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A method of packing a chromatographic medium in a longitudinally extending chromatographic tube having a first end and a second end, the second end being opposite the first end and closed, the method comprising:

placing the chromatographic medium in the chromatographic tube;

inserting a piston into the tube, the chromatographic medium being between the piston and the closed second end of the tube;

placing a pushing assembly adjacent the piston, the pushing assembly having a spring, a rod, and a locking mechanism adapted for permitting the piston to move in a first longitudinal direction toward the closed second end of the tube and for preventing the piston to move in a second longitudinal direction toward the first end of the tube;

applying a compressive force in the first longitudinal direction against the pushing assembly to move the piston toward the closed second end of the tube to compress the chromatographic medium;

removing the compressive force from the pushing assembly, the locking mechanism locking against movement of the piston in the second longitudinal direction.

2. A method as set forth in claim 1 wherein the pushing assembly includes the locking mechanism, a rod, and a spring, wherein the step of placing a pushing assembly adjacent the piston comprises positioning the pushing assembly so that the spring is positioned between the rod and the piston, and wherein the step of applying a compressive force comprises applying a compressive force against the rod to compress the spring so that the spring transmits the compressive force to the piston.

3. A method as set forth in claim 2 wherein a hydraulically operated pushing device is used to apply the compressive force to the rod.

* * * * *